(12) United States Patent
Piatrou et al.

(10) Patent No.: US 9,576,219 B2
(45) Date of Patent: Feb. 21, 2017

(54) METHOD AND SYSTEM FOR DETECTION OF CONTRABAND NARCOTICS IN HUMAN DIGESTIVE TRACT

(71) Applicant: ADANI Systems, Inc., Alexandria, VA (US)

(72) Inventors: Vadzim A. Piatrou, Minsk (BY); Vladimir N. Linev, Minsk (BY)

(73) Assignee: ADANI SYSTEMS, INC., Alexandria, VA (US)

( * ) Notice: Subject to any disclaimer, the term of this patent is extended or adjusted under 35 U.S.C. 154(b) by 40 days.

(21) Appl. No.: 14/798,926

(22) Filed: Jul. 14, 2015

(65) Prior Publication Data
US 2017/0017860 A1    Jan. 19, 2017

(51) Int. Cl.
| | | |
|---|---|---|
| G06K 9/00 | (2006.01) |
| G06K 9/48 | (2006.01) |
| H04N 7/18 | (2006.01) |
| G06T 7/00 | (2006.01) |
| G06T 3/40 | (2006.01) |
| G06T 3/60 | (2006.01) |
| G06T 3/00 | (2006.01) |

(52) U.S. Cl.
CPC ............... *G06K 9/48* (2013.01); *G06T 3/0006* (2013.01); *G06T 3/40* (2013.01); *G06T 3/60* (2013.01); *G06T 7/0032* (2013.01); *G06T 7/0038* (2013.01); *G06T 7/0046* (2013.01); *G06T 7/0081* (2013.01); *H04N 7/18* (2013.01); *G06T 2207/10116* (2013.01); *G06T 2207/30092* (2013.01); *G06T 2207/30196* (2013.01)

(58) Field of Classification Search
CPC .............................. G06K 9/48; G06T 7/0046
See application file for complete search history.

(56) References Cited

U.S. PATENT DOCUMENTS

| | | | | |
|---|---|---|---|---|
| 2014/0028457 A1* | 1/2014 | Reinpoldt | .......... | G08B 13/2494 340/552 |
| 2016/0151025 A1* | 6/2016 | Gatayama | ............. | G01T 1/1603 378/20 |

OTHER PUBLICATIONS

Rashid et al (NPL: "Walking on thin ice! Identifying methamphetamine 'drug mule' on digital plain radiography, 2014, British Institute of Radiology").*

(Continued)

*Primary Examiner* — Oneal R Mistry
(74) *Attorney, Agent, or Firm* — Bardmesser Law Group

(57) ABSTRACT

A method for automated detection of illegal substances smuggled inside internal cavities of a passenger, e.g., as capsules. The method provides for an automated detection of narcotics hidden in a passenger's stomach area using pictures produced by an X-ray scanner. According to an exemplary embodiment, throughput of the scanner is increased by an automated detection algorithm, which takes less time than visual analysis by an operator. The operator is only involved in cases when narcotics are detected. The automated detection method has a consistent precision, because the effects of tiredness of the operator are eliminated. Efficiency and costs of the process are improved, since fewer qualified operators can service several scanners.

25 Claims, 20 Drawing Sheets

(56) References Cited

OTHER PUBLICATIONS

Parmar et al (NPL: "An Approach to CT Stomach Image Segmentation Using Modified Level Set Method", IIT India 2012, Springer).*

Pinto et al (NPL: "Forensic Radiology Special Feature: Review Article Radiological and practical aspects of body packing", p. 8, British Institute of Radiology, doi: 10.1259/bjr.20130500).*

Shahnazi et al (NPL: "Body Packing and Its Radiologic Manifestations: A Review Article", p. 6, DOI: 10.5812/iranjradiol.4757, Loghman Hakim Hospital, Shahid Beheshti University of Medical Sciences, Tehran, Iran).*

* cited by examiner

METHOD AND SYSTEM FOR DETECTION OF CONTRABAND NARCOTICS IN HUMAN DIGESTIVE TRACT

BACKGROUND OF THE INVENTION

Field of the Invention

The present invention relates to airport and prison security scanners, and more particularly, to a system for detection of illegal substances/narcotics smuggled inside internal cavities of a passenger or visitor to a secure facility.

Description of the Related Art

Currently, security systems at airports, secure facilities and other public areas use microwave or X-ray scanners with penetrating or reflected radiation. These scanners are used for scanning passengers (for example) and detecting prohibited or illegal objects located on a body of the passenger or inside the passenger without a manual pat down or search. A conventional scanner displays objects on an operator's screen and the operator has to perform a visual review of the screen images and to make a decision on whether to allow a person through or to perform additional manual search or scanning. However, this conventional approach is somewhat slow, inefficient and is heavily dependent on the operator who can get tired by the end of his shift, and make wrong decisions and miss some objects on the screen. Therefore, a method for automated analysis and detection of prohibited objects and illegal substances is needed.

Existing systems and methods are inefficient for detection of narcotics being smuggled inside person's stomach. U.S. Pat. No. 8,437,556 describes shape-based object detection and localization system. The separate objects are segmented on an image and are classified based on geometrical parameters and appearance similarity to suspected objects. This method cannot be used for detection of drugs located inside the stomach cavity, because the images cannot be segmented due to a low contrast of the drug filled packets with the surrounding area of the stomach. In other words, these packets cannot always be reliably distinguished on the image without considerable manual effort.

US Patent Publication No. 20150010128 discloses a method for finding liquids inside the laggage. The proposed method uses segments of the objects and uses their atomic number acquired by dual-energy method. However, this approach cannot be used for detection of drugs located inside the stomach. An automated method for detection of hidden objects using microwave scanners is described by U.S. Pat. No. 8,774,461. The proposed method analyses a set of consecutive images of a surface of a human body. However, this method cannot be applied to detection of drugs located inside a human body, because the method is based on detection of humps and valleys on a image of a surface of a human body.

Another automated detection method is disclosed in publication by Mery, D., Automated Detection of Welding Discontinuities without Segmentation, *Materials Evaluation*, p. 657-663 (2011). This method detects welding defects by a sliding window method. However, the stomach area has many abnormalities and produces visual noise, which does not provide reliable information without additional filtering of data provided by the window classifier.

Accordingly, there is a need in the art for an effective method for an automated detection of illegal substances smuggled inside internal cavities of a human being, particularly inside his digestive tract.

SUMMARY OF THE INVENTION

The present invention relates to security scanners, such as those at airports and prisons/secure facilities, and more particularly, to a system and method for an automated detection of illegal substances smuggled inside internal cavities of a human being that substantially obviates one or more of the disadvantages of the related art.

In one aspect, there is provided a method for automated detection of illegal substances smuggled inside internal cavities of a passenger. The method provides for an automated detection of drugs hidden in a passenger's stomach area using pictures produced by an X-ray scanner. According to an exemplary embodiment, throughput of the scanner is increased by an automated detection algorithm, which takes less time than visual analysis by an operator. In the exemplary embodiment, the operator is only involved in cases when drugs are detected. The automated detection method has a consistent precision because the effects of tiredness of the operator are eliminated. All data from the image is used including analysis of the private body parts that may not be displayed to the operator. Efficiency and costs of the process are improved, since fewer qualified operators can service several scanners.

Additional features and advantages of the invention will be set forth in the description that follows, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE ATTACHED FIGURES

The accompanying drawings, which are included to provide a further understanding of the invention and are incorporated in and constitute a part of this specification, illustrate embodiments of the invention and together with the description serve to explain the principles of the invention.

DETAILED DESCRIPTION OF EMBODIMENTS OF THE INVENTION

Figure 1:
FIG. 1 illustrates an exemplary image that can processed by the drug detection method.

Reference will now be made in detail to the embodiments of the present invention, examples of which are illustrated in the accompanying drawings.

An algorithm, system and computer program for a method of automated detection of drugs hidden in a passenger's stomach area using pictures produced by an X-ray scanner. According to an exemplary embodiment, throughput capacity of the scanner is increased by an automated detection algorithm, which takes less time than visual analysis by an operator. In the exemplary embodiment, the operator is only involved in cases when drugs are presumed to be detected. The automated detection method has a consistent precision because the effects of tiredness of the operator are eliminated. All data from the image is used, including analysis of the private body parts that might not be displayed to the operator. Efficiency and costs of the process are improved, since fewer qualified operators are required for servicing the scanners.

According to the exemplary embodiment, a detection algorithm can be used to classify any images by detection of small object or several objects in particular area where the size of the individual objects is small relative to the size of the area. In order to find drugs hidden in the stomach area, additional images derived from the original image are used. These additional images can be used in logarithmic and contrasted form. Also, saliency map image is used.

The logarithmic picture reflects a degree of absorbing of transmitted radiation by different body parts and objects. The contrasted image visualizes small details and provides reliable image property data. A saliency map of the image allows for defining objects of a given scale. The parameters of the saliency map are selected in order to visualize the drug-filled pouches (or bags) inside the stomach area.

In one embodiment, a sliding window method can be used. A detection window, which runs across the entire stomach area, is classified. The areas with drugs need to be distinguished not only from other fairly consistent stomach portions, but also from low-contrast anatomical parts (e.g., ribs, spine, pelvic bones, etc.) as well as from high-contrast non-anatomical objects. According to the exemplary embodiment, classification of windows for presence of drugs in the stomach area is achieved as follows:

filtering of low-contrast anatomic areas uses their positioning defined by relative coordinates that are symmetrical relative to the body symmetry axis;

in order to filter high-contrast non-anatomic objects, a search of these objects is implemented using a corresponding classifier and a subsequent removal of the areas occupied by the non-anatomic objects is executed.

The relative coordinates (see FIG. 9) allow to group anatomic objects of a certain type for different people because they have close values of coordinates. These coordinates are symmetrical relative to the body symmetry axis and the anatomic objects located on the left and on the right of the spine also have close values of coordinates. Grouping of different types of anatomic objects provides for efficient objects filtering for classification of windows with drugs (or suspected drugs).

Detection of high-contrast objects is achieved by segmentation of suspected areas and by checking these areas by high-contrast classifier. In order to improve a window classifier, features invariant under rotation and constructed from periodic properties (e.g., Fourier and cosine transform coefficients) are used. The features invariant to rotation guarantee that the same frequency in any direction (e.g., horizontal or diagonal) produces the input into one common property instead of affecting several coefficients, as would be the case for regular periodic features.

However, precise detection of drugs requires construction of an image classifier based on individual window classification data. The image classification can use a method for anomalies detection since a number of images without drugs are substantially higher than of those with drugs in them. A set of image features is created based on window classification data. This method considers that the images without drugs in then have multivariate normal distribution of features. The images with drugs are considered to be an "anomaly" because they have abnormal distribution of features and can be classified by selection of a threshold value of a distribution function.

Figure 4:
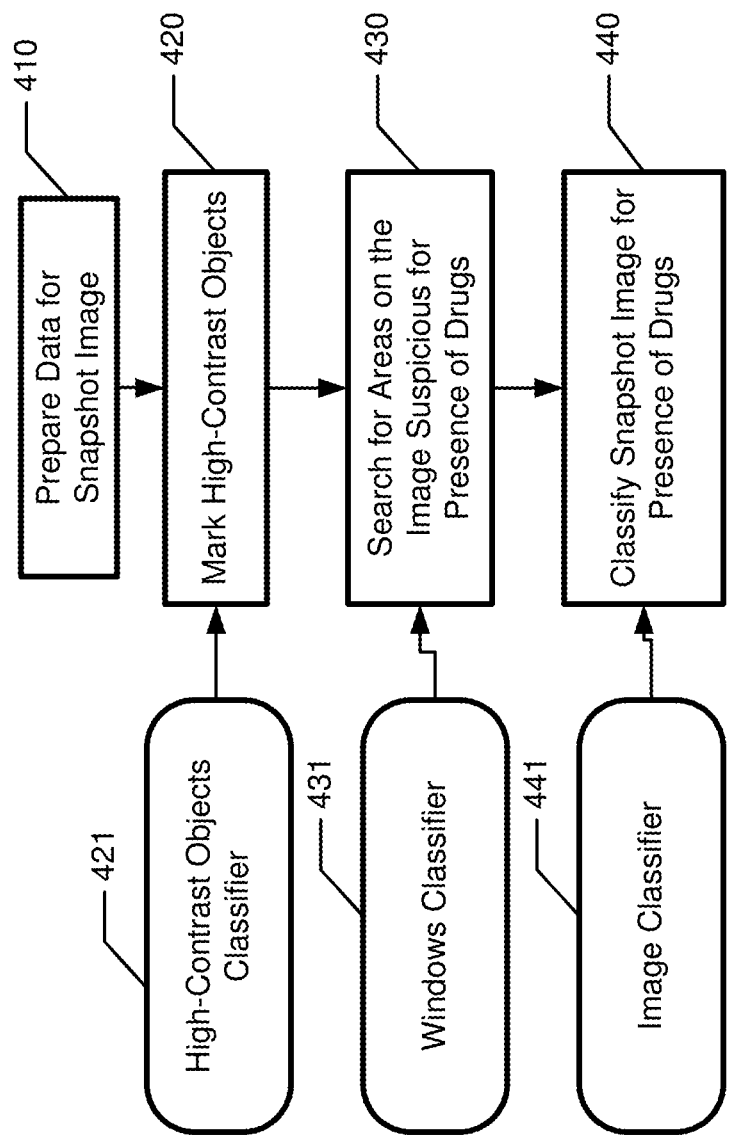
FIG. 4 illustrates an algorithm for drug detection, in accordance with the exemplary embodiment.
Figure 5:
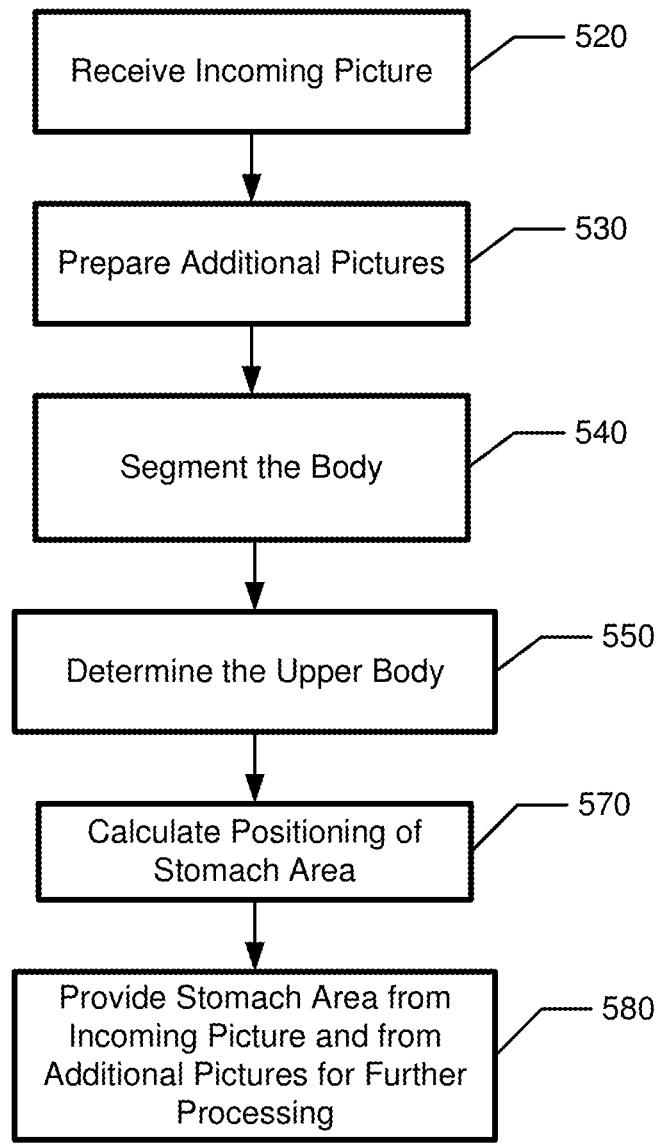
FIG. 5 illustrates a flow chart for loading a snapshot for analysis and preparing data for subsequent steps of an algorithm.
Figure 7:
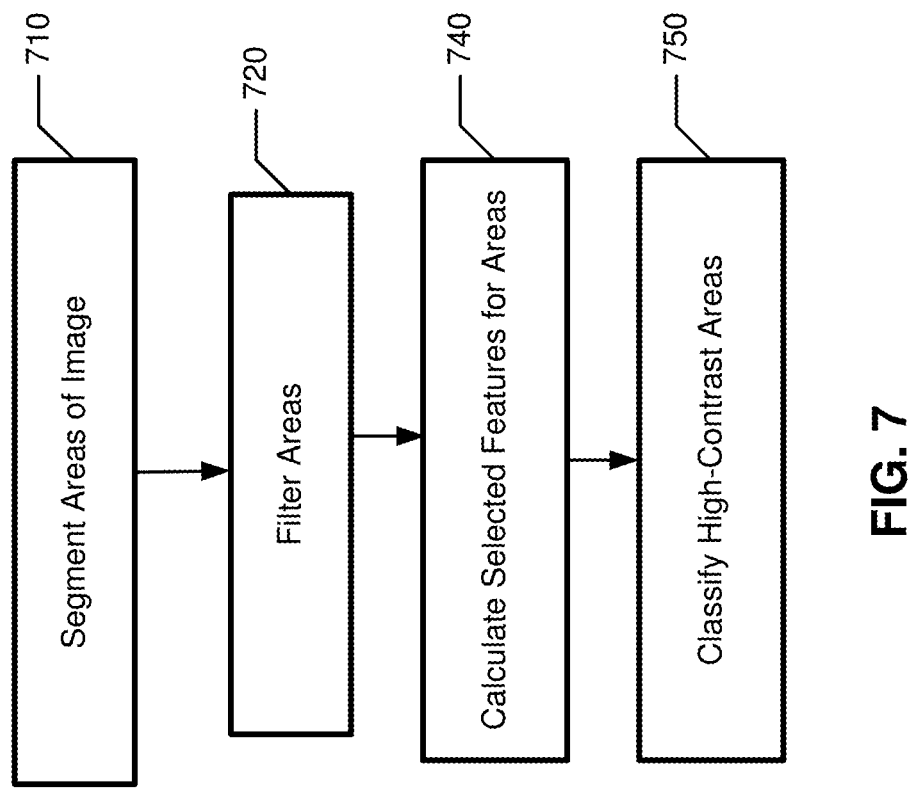
FIG. 7 illustrates classification of high-contrast objects in a stomach area on new images.
Figure 11:
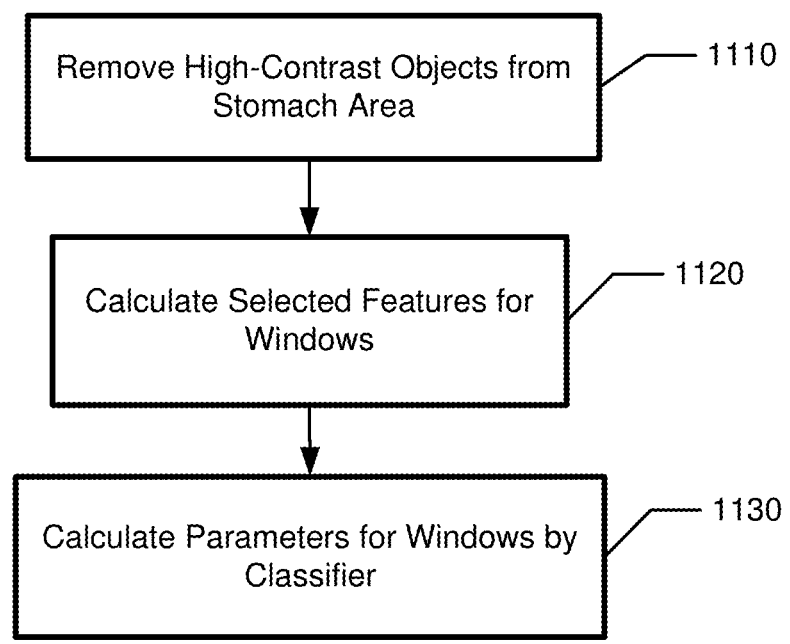
FIG. 11 illustrates a flow chart for searching for windows suspected for containing drugs.
Figure 16:
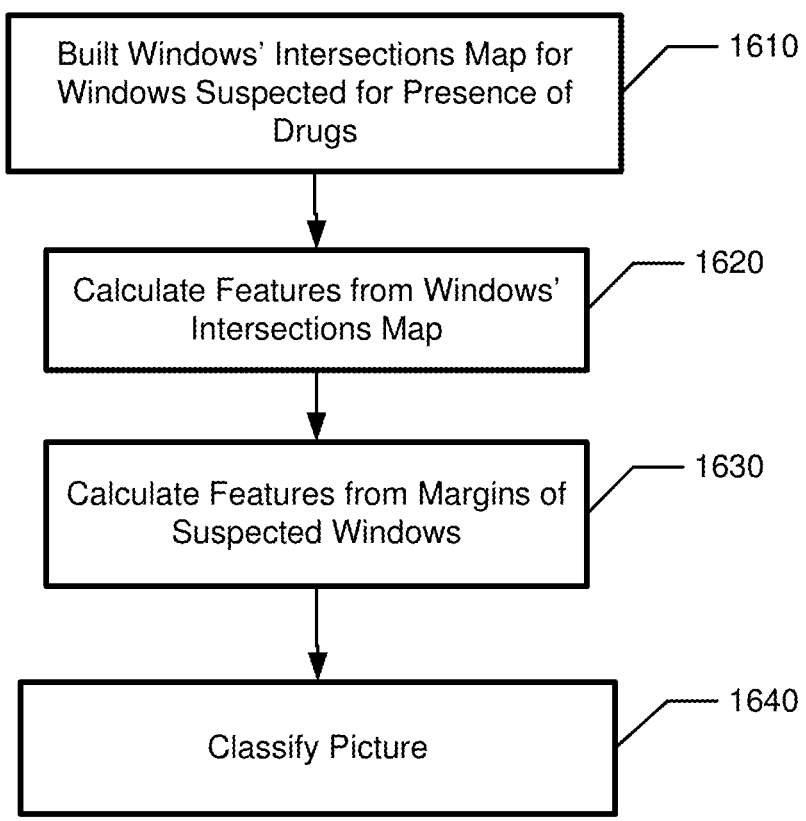
FIG. 16 illustrates a flow chart for classifying the image for presence of drugs.

FIG. 4 illustrates an algorithm for drug detection, in accordance with the exemplary embodiment. In step 410, a snapshot is loaded and a data required for analysis is prepared (as shown in FIG. 5). In step 420, high-contrast objects are segmented for classification by a high-contrast object classifier 421 (as shown in FIG. 7). In step 430, the high-contrast objects are removed from the original image and from the additional images. Then, the sliding window method is applied. A search for areas on the image suspicious for presence of drugs is performed by a classifier 431 (as shown in FIG. 11). In step 440, the common features are calculated for the stomach area and classified for presence of drugs by the image classifier 441 (as shown in FIG. 16).

FIG. 5 illustrates a flow chart of a step of an image processing algorithm, which includes loading a snapshot for analysis and preparing data for subsequent steps of an algorithm. The incoming picture is received in step 520 and processed for additional images (logarithmic, contrasted and a saliency map) in step 530. The saliency map is an image processed based on a human attention system. This system considers that a human eye fixates on different parts of a complex image sequentially. The exemplary algorithm uses a saliency map focused on a background with a scale 12, 24 and 48 in order to reflect drug containers of 10-20 pixels in size.

Figure 2:
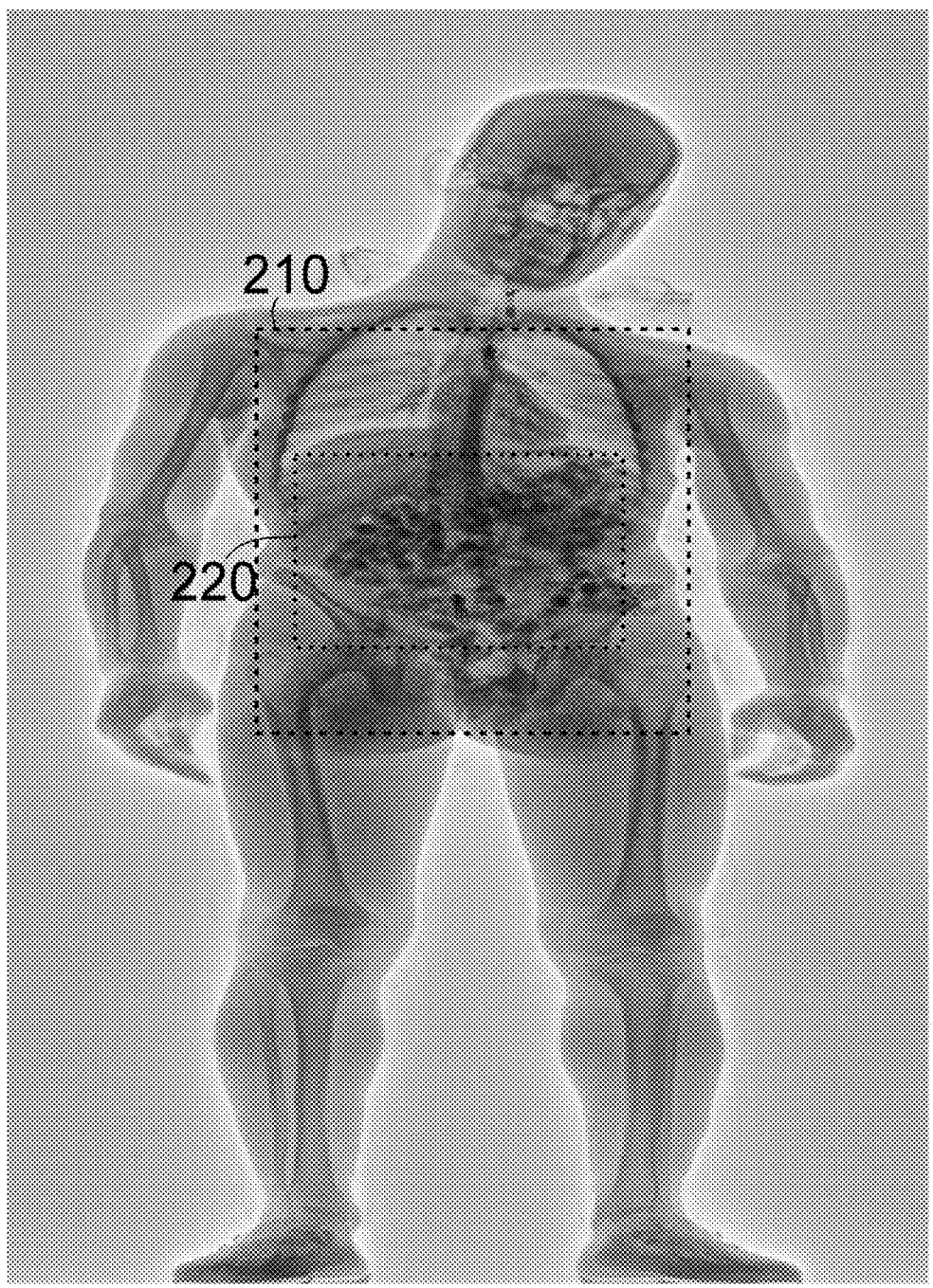
FIG. 2 illustrates an example for detection of the upper body and determination of the stomach area.

Contrasting of an image is implemented by processing an image in order to create better local contrast between adjacent areas of the image. A local statistics for minimums, maximums and average values in each small area of the image are collected in order to use this data for redistribution of intensity of pixels of the areas. In step 540, the human body is segmented on a logarithm image based on a fixed threshold. The threshold is selected on a large number of images, so the body is almost completely separated from the background. In step 550, an upper body is determined by one of the known methods (see 210 in FIG. 2). One method determines maximum area of intersection of lines and columns where a number of body pixels exceed a threshold.

Another method finds an upper body borders' contours using a pre-constructed two-dimensional model. Then, the contour is approximated by a vertically located rectangle. The upper body is determined as a rectangular area with vertical and horizontal coordinates of upper left point $x_{upper}$ and $y_{upper}$, width $w_{upper}$ and height $h_{upper}$. Then, in step 570, a stomach location (see 220 in FIG. 2) relative to the upper body is calculated as:

$$x_{st}=x_{upper}+w_{upper}*k_x;$$

$$y_{st}=y_{upper}+h_{upper}*k_y;$$

$$w_{st}=w_{upper}*k_w;$$

$$h_{st}=h_{upper}*k_h;$$

where $x_{st}$ and $y_{st}$ are coordinates of an upper left point of the stomach area and $w_{st}$ and $h_{st}$ are width and height of the area. The parameters $k_x$ and $k_y$ reflect relative offset from the upper left corner of the upper body area and $k_w$ and $k_h$ are relative width and height of the stomach area. All of the offset parameters are set relative to the width and the height of the upper body area. The parameters $k_x$, $k_y$, $k_w$ and $k_h$ are selected on a large set of snapshots in such a way that the stomach area determined by the above formula closely matches the stomach area marked by an expert on most of the snapshots. In step 580, the stomach area is derived from the incoming image and from the additional images for further analysis.

Figure 6:
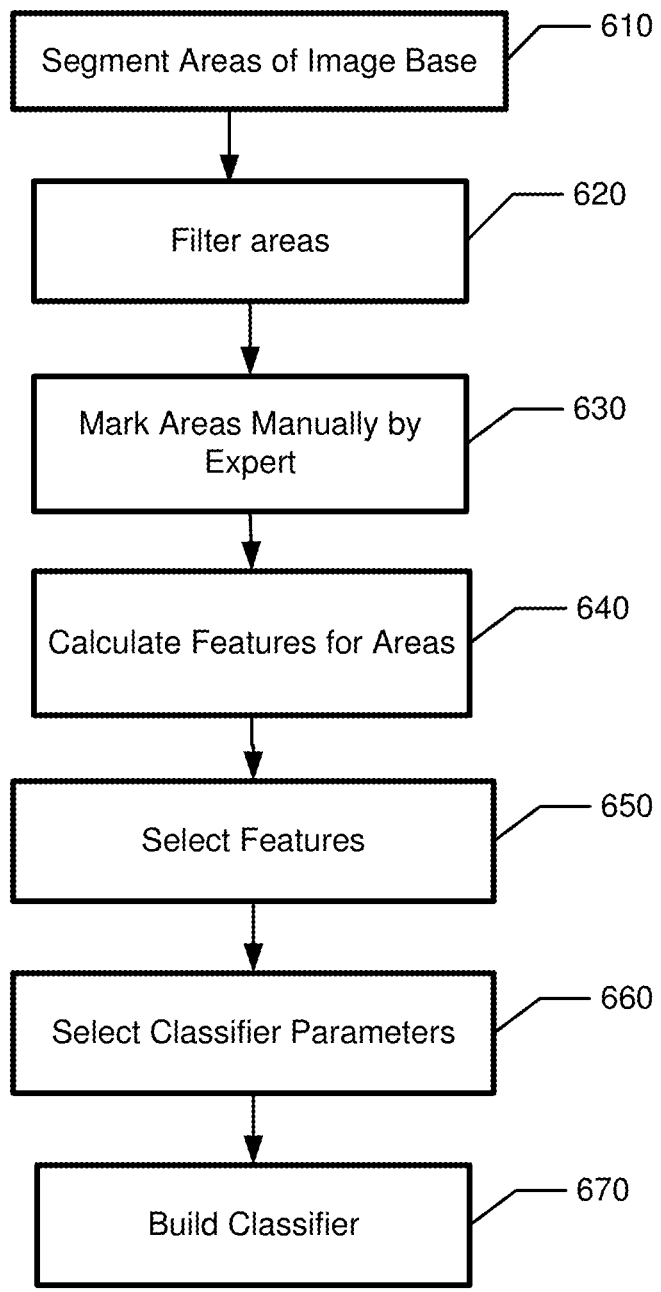
FIG. 6 illustrates a flow chart for building (or training) a classifier for high-contrast objects.

FIG. 6 illustrates a flow chart for building (or training) a classifier for high-contrast objects. According to the exemplary embodiment, marking of high contrast areas is implemented in order to eliminate some areas from further analysis for drugs detection. After the high-contrast areas are removed from the stomach area, only anatomic areas and the drug filled containers (if present) along with other low-contrasts areas are left in the image of the stomach area. Thus, this step simplifies drugs detection because a number of non-anatomic objects are reduced. Training of the classifier depicted in FIG. 6 is performed on a training set of snapshots.

Figure 8:
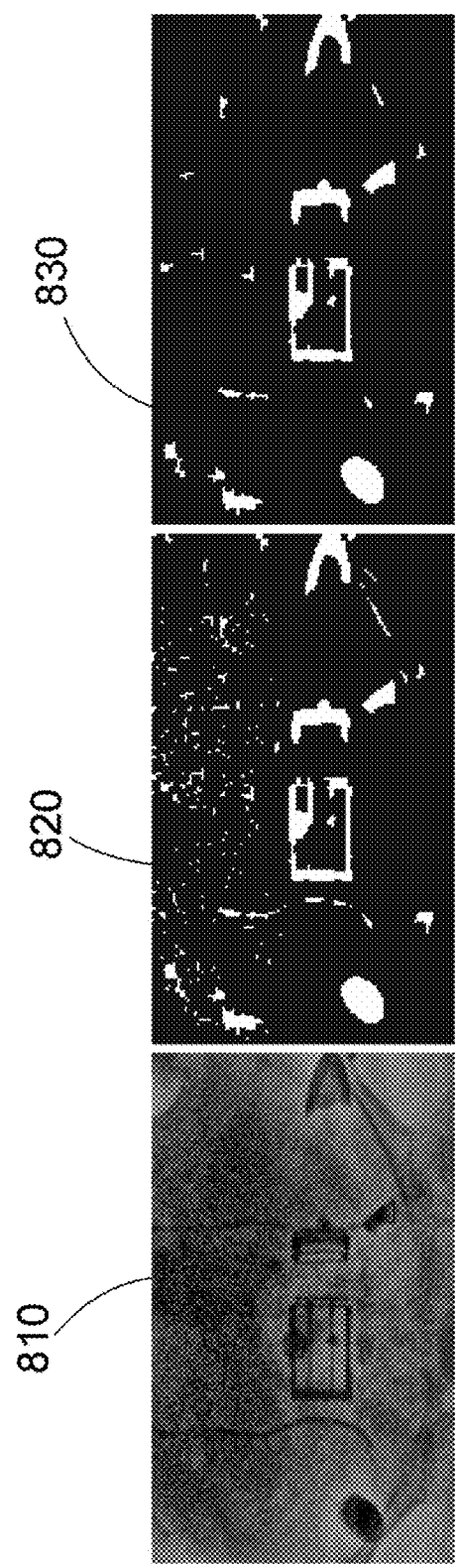
FIG. 8 illustrates an example of segmentation of areas of a scanned image.

In step 610, stomach areas of training images are segmented into suspected high-contrast areas and a background by using a global threshold on saliency map of the logarithm image focused on the background with the scale of 12, 24 and 48. The threshold is selected so that the high-contrast objects match closely the objects selected by the expert. Then, the images are subjected to a morphological connection of areas by square elements (size 3×3). This connection evens out the object edges and fills background pixels inside the objects. An example of segmentation of areas of the image is depicted in FIG. 8 (see 810 and 820).

Figure 9:
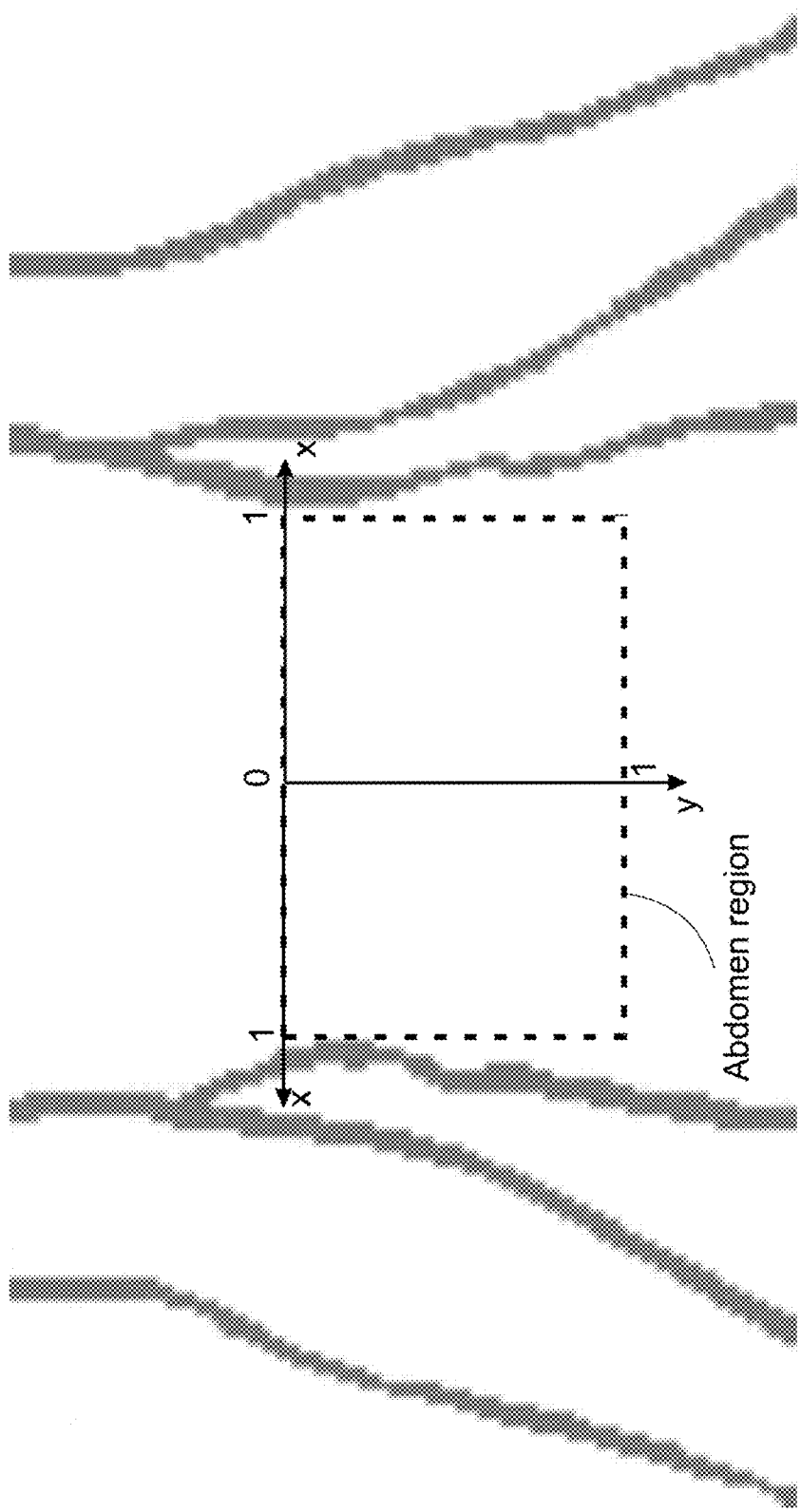
FIG. 9 illustrates relative vertical and horizontal coordinates of a center of an area of the stomach.

In step 620, filtering out small objects is implemented using minimal linear size and area of the object. The size filters are selected in such a way that noise areas of a size approaching the scanner resolution are filtered out. An example of the segmented areas after filtering is depicted in FIG. 8 (see picture 830). In step 630, manual marking of the high contrast objects by an expert is performed. All visible non-anatomic objects located in the stomach area that have intensity contrast compared to the background equals or larger than the intensity for the object are marked. Then, in step 640, a set of intensity and geometric features is calculated and selected (in step 650) on a mask defined by the segmented area for the original and additional images. The geometric features are:

- a relative vertical coordinate of a center of the area (see FIG. 9) calculated as a fraction of an average of a row numbers of all area points of the stomach over the height of the stomach;
- a relative horizontal coordinate of the center of the area (see FIG. 9). An average column numbers of the area points are calculated. Then, a distance from the calculated center to the middle of the stomach is calculated. A fraction of the distance over a half of stomach width is used as the horizontal coordinate property;
- sizes—length of the area along a horizontal and a vertical directions;
- an area—a number of pixels inside segmented area;
- a perimeter—a number of pixels located on the border of the area and the background;
- geometric Hu features ((1962), Visual pattern recognition by moment invariants, *Information Theory, IRE Transactions on*, V. 8(2), P. 179-187)—i.e., area features invariant relative to translations, scale and rotations;
- geometric Flusser features ((1993), Pattern recognition by affine moment invariants, *Pattern Recognition*, V. 26(1), P. 167-174) that are invariant relative to common affine transformations;
- geometric Gupta features ((1987), Contour sequence moments for the classification of closed planar shapes, *Pattern Recognition*, V. 20(3), P. 267-272);
- i.e., features of area borders invariant to translations, scale and rotations.

The intensity features are:

- basic features of intensity, gradient and Laplacian i.e., integral, average and maximum values);
- Haralick features describing texture ((1973), Textural Features for Image Classification, *Systems, Man and Cybernetics, IEEE Transactions on*, V. SMC-3(6), P. 610-621);
- Gabor features used for texture description on different scales and in different directions (Kumar, A., and G. K. H. Pang (2002), Defect detection in textured materials using Gabor filters, *Industry Applications, IEEE Transactions on*, V. 38(2), P. 425-440);
- Hu features (see above) calculated by the intensity in a given area (instead of a binary area image).

In addition to the above features, square, cube or higher power values of the features can be used. A large number of features make for more precise classification until a number of features matches a number of data for which the classifier is constructed. If a number of features are increased further, an overfitting effect takes place—i.e., the classifier is improved on a training set of data while the results on a test set of data decrease. In step 650, a set number of best classifier features are selected out of all features based on manually selected marks. A Sequential Forward Selection method can be used in combination with Fisher criteria. Then, the best parameters for the classifier are selected based on the features in step 660. Only the selected features and the best classifier parameters are used for building the classifier in step 670 and for further classification of high-contrast objects.

A classification algorithm can use standard methods such as, for example, a support vector machine. Selection of classifier parameters can be implemented by a sliding control method for going through various sets of parameters. The parameters that provide for best classification results of high-contrast objects are used for construction of the classifier in step 670.

Figure 12:
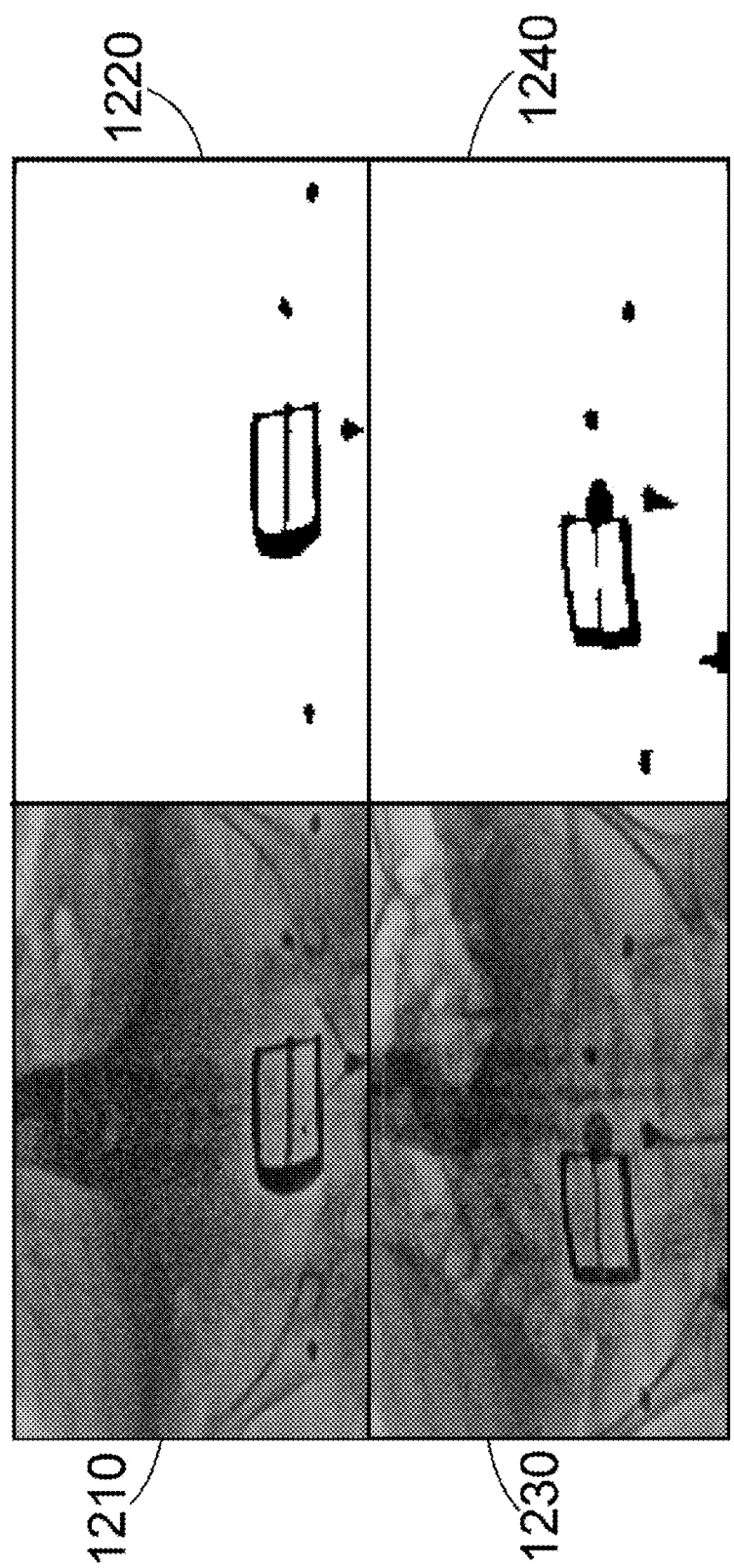
FIG. 12 illustrates contrasted areas of the stomach and maps of the same areas shown after elimination of the high-contrast objects.

Classification scheme of high-contrast objects in a stomach area on new images is depicted in FIG. 7. In step 710, the areas of the image that have suspected high-contrast objects are segmented. In step 720, the areas are filtered by size and area (as described above). A set of selected features (geometric and intensity) used for construction of the classifier are calculated on the new image in step 740. Note that the calculation is performed for incoming (i.e., original) and for additional images on a mask defined with segmented areas. The calculated features are used for classification of the areas by the constructed classifier in step 750. Classification results for high-contrast objects are shown in FIG. 12. The classifier checks segmented areas for high-contrast objects.

Figure 10:
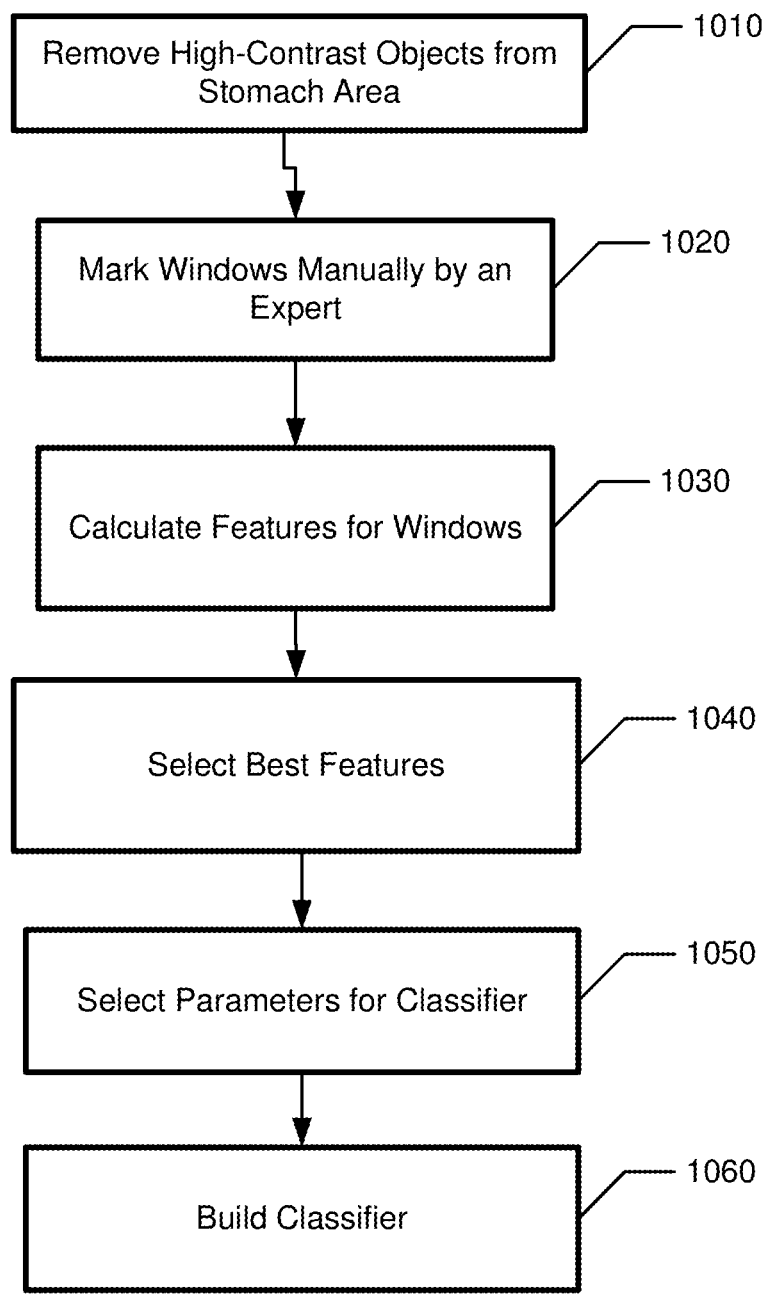
FIG. 10 illustrates a flowchart for building a classifier for windows with drugs.

FIG. 10 illustrates a flowchart for building a drugs classifier for windows. In step 1010, high-contrast objects are removed from a stomach area. Windows are marked by an expert in step 1020. Features for windows are calculated in step 1030. Unlike high-contrast objects, the geometrical features are not used. Instead, Fourier and cosine transform coefficients along with local binary patterns are used. Best suited features are selected in step 1040. Then, the parameters for the classifier are selected based on the features in step 1050. Selected features and the best classifier parameters are used for building the windows classifier in step 1060.

FIG. 11 illustrates a flow chart for searching for windows suspected for containing drugs. According to the exemplary embodiment, a search for suspicious areas is implemented using the sliding window method, where a window size is selected to be twice the size of the typical container with drugs in images used for training of the classifier. A horizontal offset and a vertical offset for neighboring windows are selected to be two times smaller than their size. In step 1110, the high-contrast objects are removed from the stomach area. The process calculates selected features for windows in step 1120. In step 1130, windows' classes and margins are obtained using the constructed windows classifier.

According to the exemplary embodiment, the classifier can calculate classes—drugs or background, to which the analyzed window belongs. The classifier also returns a classification reliability value, calculated as a margin from a point described by window features to a hyper-plane dividing the classes in a features space. For example, two windows have offsets −0.5 and −1.2. Negative values mean that these windows are suspected for presence of drugs. Two other windows can have positive offsets 0.2 and 0.7. They are classified by the classifier as a background. Margins are used at the final stage for classification of the entire image for presence of drugs.

Figure 13:
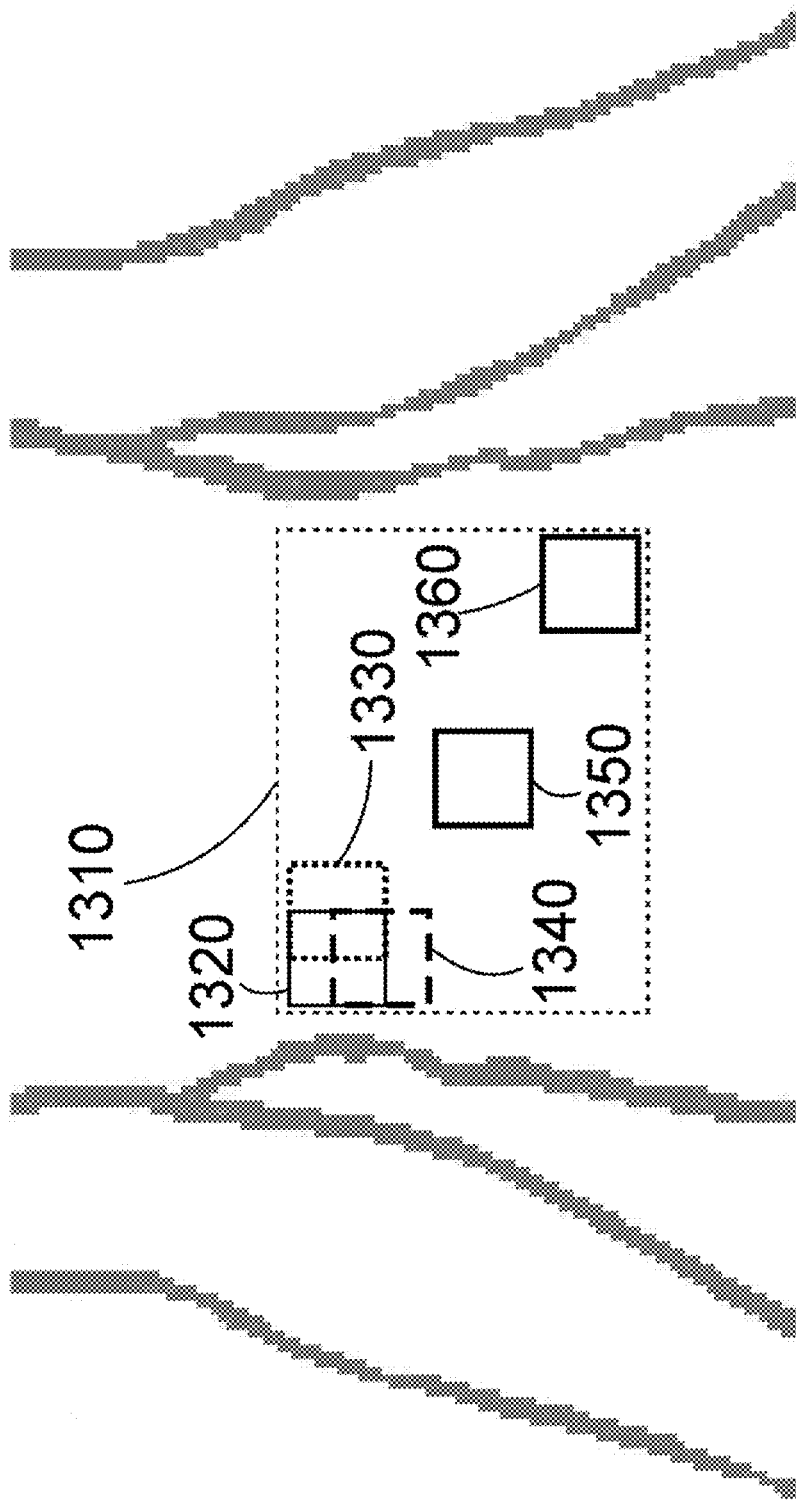
FIG. 13 illustrates an example of locations of the detection window.

An example of locations of the detection window is shown in FIG. 13. An initial position 1320 of the window is shown in the upper left corner of the stomach area 1310. This detection window needs to be checked for presence of drugs. Once this window is checked, the next window 1330 is analyzed. After the detection window reaches the right edge of the stomach area 1310, the window moves to the left position 1340 in the second row. Thus, the detection window 1350 has to go over the entire stomach area 1310. The last position of the window 1360 is located in the bottom right corner of the stomach area 1310.

In order to classify the windows containing drugs, an appropriate classifier needs to be trained. Training of the classifier is depicted in FIG. 10. This step is implemented on the basis of a new image training set. The images have to differ from the images used for training the high contrast objects classifier in order to be classified appropriately. First step in constructing windows classifier is preparing data for a training set of images (see FIG. 5) and searching for the high-contrast objects as shown in FIG. 7. Then, the areas with high-contrast objects are eliminated. FIG. 12 illustrates contrasted areas of the stomach 1210 and 1230 and maps for the same areas (1220 and 1240) shown after elimination of the high-contrast objects. The processed areas 1220 and 1240 are used for further analysis for drugs.

In order to account for invariance to rotation for periodic parameters, the additional features can be calculated, for example, for Fourier and cosine transform coefficients. Periodic coefficients f(i,j) can be used, where i and j are indexes of rows and columns of a square matrix of coefficients of a size S. If the invariant to rotation periodic parameters are used, the same horizontal, vertical or diagonal periodicity have to produce an input into one common property—not into different coefficients as in the case with the Fourier and cosine transform coefficients.

A number of invariant to rotation features equals to the length of a diagonal of the coefficient matrix rounded to the highest number:

$$nRI=\mathrm{ceil}(S\sqrt{2}),$$

where ceil( ) is rounding up function.

In order to calculate invariant features for each coefficient, a distance to the upper left pixel of the coefficient matrix is calculated as:

$$r=\sqrt{(i-1)^2+(j-1)^2}.$$

Then, the coefficient f(i,j) is added with a certain weight to the two invariant to rotation features:

$$fRI(\mathrm{floor}(r))=fRI(\mathrm{floor}(r))+f(i,j)\cdot(\mathrm{ceil}(r)-r),$$

$$fRI(\mathrm{ceil}(r))=fRI(\mathrm{ceil}(r))+f(i,j)\cdot(r-\mathrm{floor}(r)),$$

where fRI—calculated features invariant to rotation, floor ( )—rounding to nearest lower value function.

Additional features comprising a sum of features invariant to rotation can be calculated as:

$$fRISUM(p,q)=\sum_{j=p}^{q}fRI(j).$$

An aggregate number of these features is calculated as:

$$nRISUM=\tfrac{1}{2}nRI\cdot(nRI-1).$$

Figure 14:
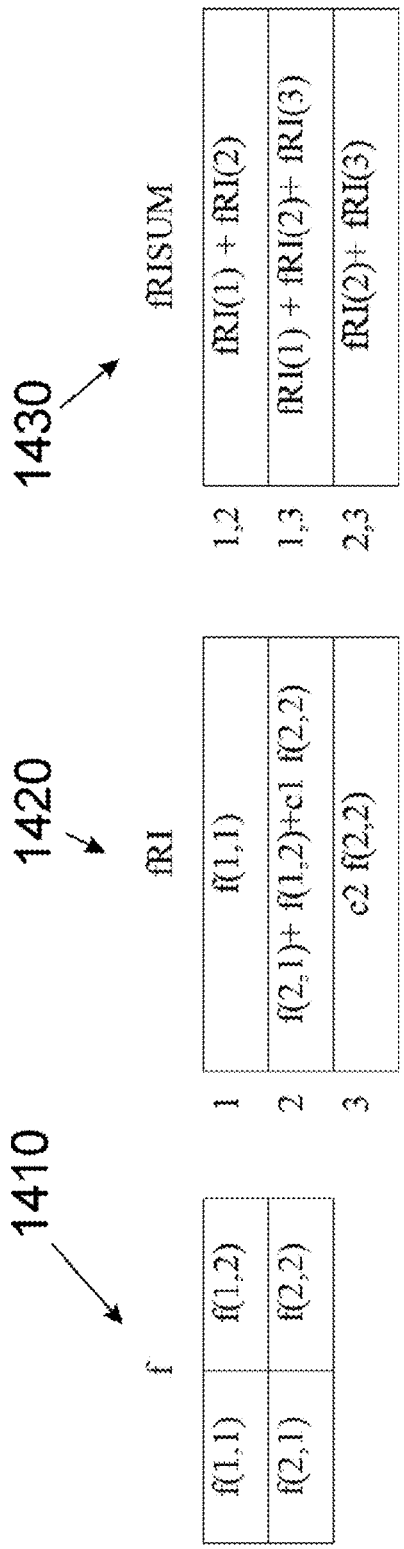
FIG. 14 illustrates an example of calculation of invariant to rotation features for periodicity for coefficients matrix of a size 2×2.

A goal of using these features is uniting the coefficients with similar frequencies for subsequent use in classification, because a meaningful property can be a sum of neighboring elements (instead of a single component of the invariant property). An example of calculation of invariant to rotation features for periodicity for coefficients matrix of a size 2×2 is shown in FIG. 14. The coefficients 1410 are included into the coefficients 1420 invariant to rotation as weighted sum calculated by above formulas. Since the size for the periodic property is S=2, the number of such features is 3. A first column of coefficients 1420 contains indexes of invariant features and a second column contains a formula for calculating these features from the original ones 1410, where c1 and c2 are factors for the coefficients f(i,j) from the above formulas.

Likewise, for the sums of features invariant to rotation, in table 1430 the left column contains indexes of sum property and the right column contains example of calculations of component of the sum property using single invariant features. Increase of a number of features enhances the accuracy of classification. Selection of a number of best suited features from all the calculated features is implemented by, for example, Sequential Forward Selection method.

Figure 15:
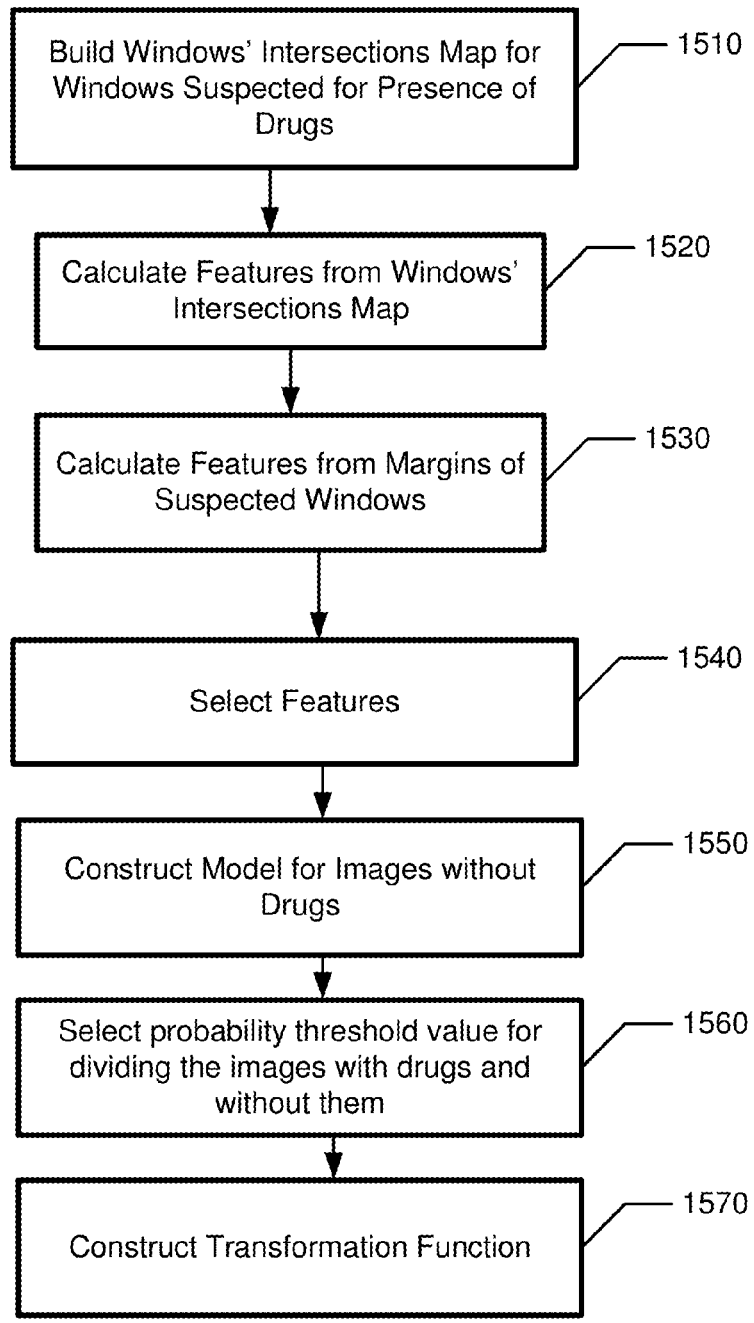
FIG. 15 illustrates a flow chart for constructing the image classifier.
Figure 17:
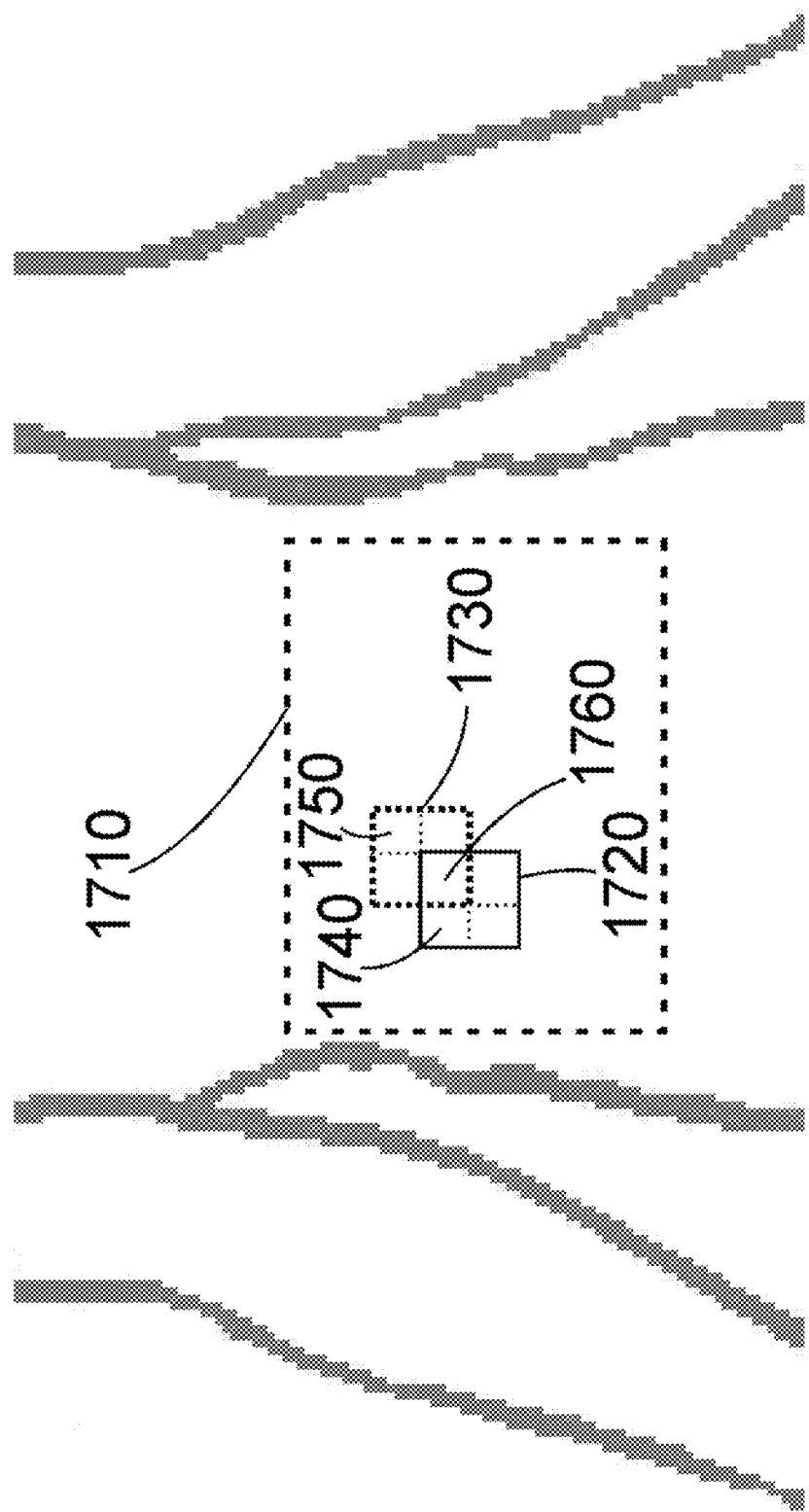
FIG. 17 illustrates position of sub-windows suspected for presence of drugs in a stomach area.

FIG. 15 illustrates a flow chart for constructing the image classifier. In step 1510, the process builds windows' intersections map for windows suspected for presence of drugs. In step 1520, the process calculates features from a windows' intersections map. In step 1530 the process calculates features from margins of the suspected windows. In step 1540, the most suitable features are selected. In step 1550, the process constructs a model for images without drugs. In step 1560, the process selects a probability threshold for dividing the images with drugs and without them. In step 1570, the process constructs a transformation function. The data about position of windows 1720 and 1730 (see FIG. 17) suspected for presence of drugs in a stomach area 1710 is used for construction of windows' intersection map.

All windows have the same size. Windows' offsets in horizontal and vertical directions are two times smaller than the size of the window. Thus, a window can be divided into four sub-windows of half the original size. If the suspected window has all sub-windows marked, then each sub-window in the stomach can be marked 0, 1, 2, 3 or 4 times. For example, in FIG. 17 the sub-windows 1740 and 1750 are only marked once, while sub-window 1760 is marked twice. A number of sub-windows marked a certain number of times can be used as an efficient criteria (aggregate feature) for separating the images with and without drugs.

Based on an intersection map, the following can be determined:
 a number of windows classified for drugs;
 a number of sub-windows with intersection 1;
 a number of sub-windows with intersection 2;
 a number of sub-windows with intersection 3;
 a number of sub-windows with intersection 4.

Another set of data that can be used for creating image aggregate features are the margin values from a hyper-plane dividing classes in features space. The features are produced during classification of the stomach area windows. The margin reflects the probability that the selected window contains drugs. The large margins indicate a higher probability of drug presence. The following aggregate features can be constructed from the margin values for separating the images with drugs and the ones without drugs:
 a sum of margins to the dividing hyper-plane;
 an average value of the margins to the dividing hyper-plane;
 a standard deviation of the margins to the dividing hyper-plane;
 1-st maximum absolute value of the margin to the dividing hyper-plane;
 2-d maximum absolute value of the margin to the dividing hyper-plane;
 3-d maximum absolute value of the margin to the dividing hyper-plane;
 4-th maximum absolute value of the margin to the dividing hyper-plane;
 5-th maximum absolute value of the margin to the dividing hyper-plane;
 a sum of 5 maximum margins to the dividing hyper-plane; and
 an average value of 5 maximum margins to the dividing hyper-plane.

The second step of teaching the classifier is selection of best suited features from the above list. For example, the features that are linearly dependent from other features are discarded. According to the exemplary embodiment, a model for images without drugs is constructed using selected features. The model is implemented as a multivariate normal distribution with a zero average value for all selected features, since for most images without drugs the features should have zero values. In order to construct the model, a training set of images without drugs is used. The selected features (from the above list) are calculated. A multivariate normal model for images without drugs is constructed.

The multivariate normal distribution is described by a covariance matrix, which is calculated as:

$$\sum = \frac{X^T X}{m},$$

Where m—is a number of images in a training set, X—matrix of features with m rows containing selected features for the images. The resulting covariance matrix is used in a formula for calculation of the probability f(x) of image being normal (i.e., does not contain drugs):

$$f(x) = \frac{1}{(2\pi)^{n/2} |\Sigma|^{1/2}} \cdot \exp\left[-\frac{1}{2} x^T \Sigma^{-1} x\right],$$

Where x—a row of aggregate features of the analyzed snapshot. If the calculated value of f(x) approaches the maximum, it indicates the snapshot is normal—i.e., does not contain any drugs.

Maximum value of probability is as follows:

$$f_{max} = \max(f(x)) = \frac{1}{(2\pi)^{n/2} |\Sigma|^{1/2}}.$$

If the probability is close to zero (i.e., f(x)<<fmax), this means that drugs are present inside the stomach of the person whose snapshot image is being reviewed. When the classifier is constructed, a probability threshold value is selected for dividing the images with drugs and without them. A new training set of images of various types is used. Selected features (from the above list) are calculated for each of the images. The features are used in the probability calculation formula above in order to calculate a degree of similarity of the image to the images without drugs. A threshold probability value $f_\epsilon$ is selected based on analysis of probabilities values for images with drugs and the ones without drugs in order to divide the two types of images using the following rule:
 an image does not have drugs if f(x)>$f_\epsilon$,
 an image contains drugs if f(x)<$f_\epsilon$ or f(x)=$f_\epsilon$.

Figure 18:
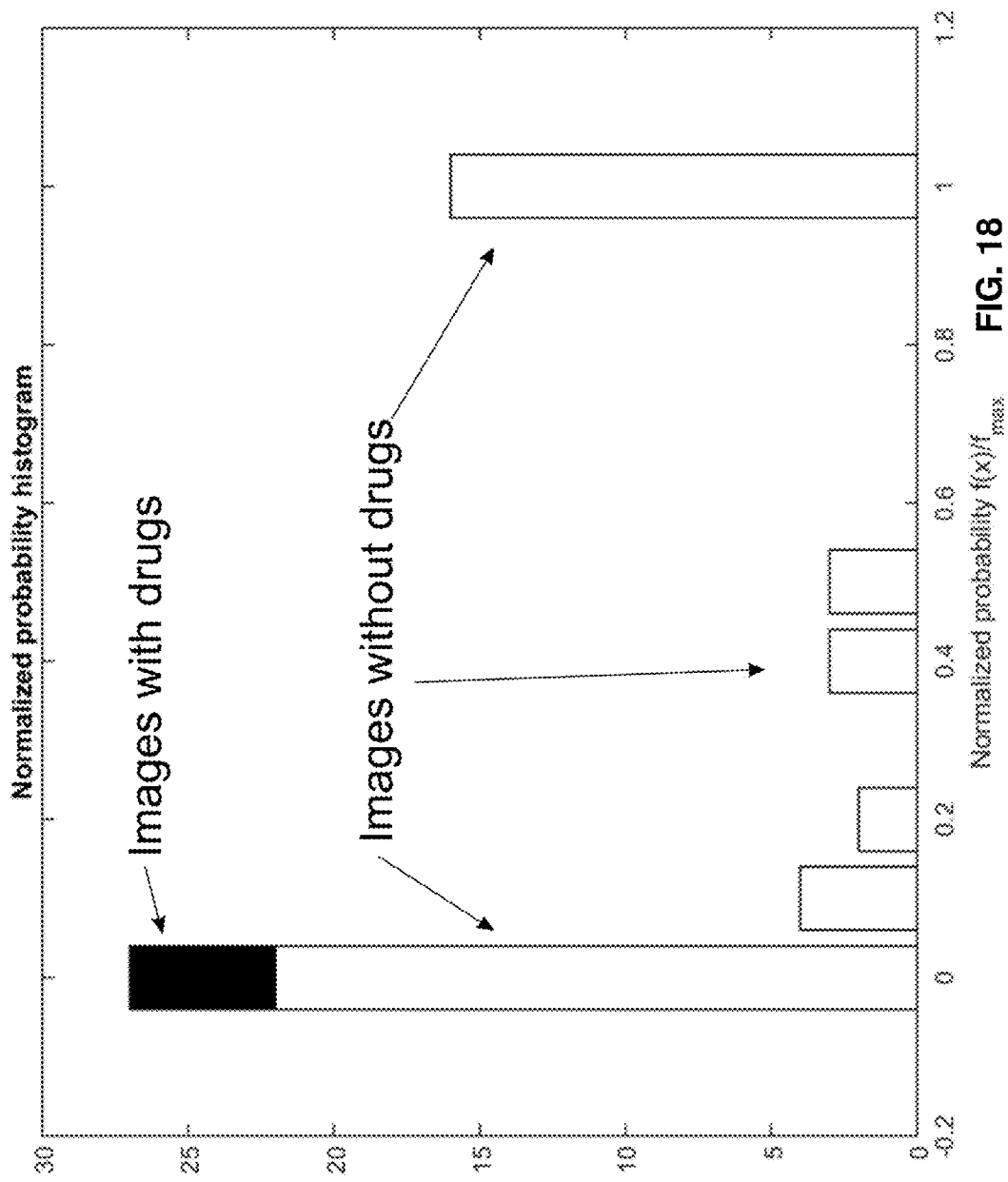
FIG. 18 illustrates a distribution of images based on probability of the image being free of drugs.

However, the threshold value $f_\epsilon$ is not convenient for interpretation because it is several orders of magnitude less than $f_{max}$. A distribution of images based on probability of the image being free of drugs is not informative as can be seen from FIG. 18. Thus, a non-linear transformation of f(x) into a new function p(x) reflecting a degree of difference of the image from the average normal (i.e., drug free) image in such a way that the following conditions are met:

$$f_{max} \rightarrow p(x) = 0\%;$$

$$f_\epsilon \rightarrow p(x) = 50\%;$$

$$0 \rightarrow p(x) = 100\%.$$

The degree of difference function is constructed in such a way that the threshold equals to 50%. The classification rule using the degree of difference from the average normal image is as follows:
   an image does not have drugs if p(x)<50%;
   an image contains drugs if p(x)>50% or p(x)=50%.
The required transformation function can have the following format:

$$p(x) = 100\% \left(1 - \left(\frac{f(x)}{f_{max}}\right)^\gamma\right),$$

where γ—a parameter of the transformation function, which is determined from the following equation:

$$\gamma = \log_{f\epsilon/fmax} \frac{50}{100}.$$

Figure 19:
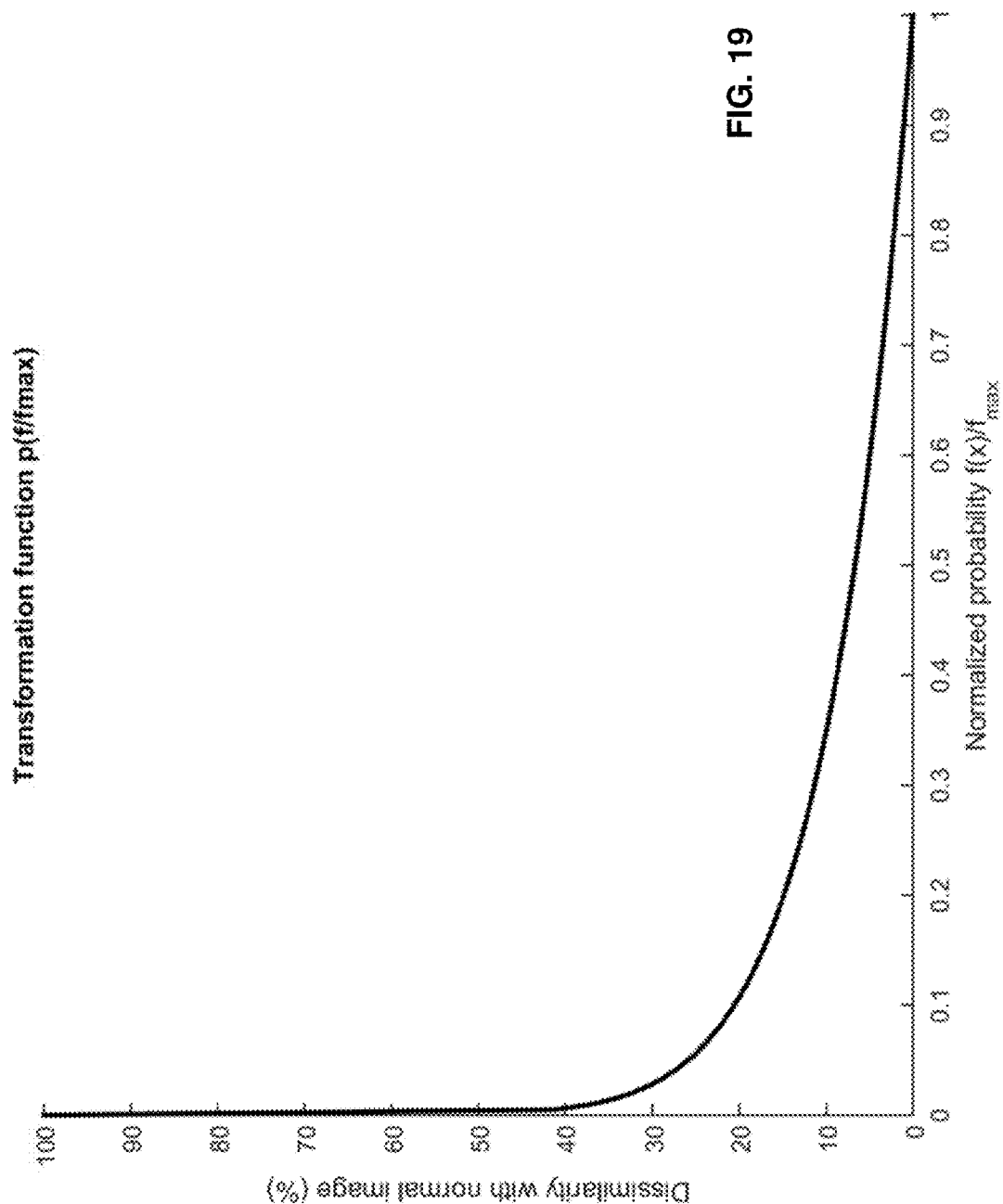
FIG. 19 illustrates an example of the transformation function $p(f/f_{max})$ with the parameter $\gamma=0.1$.
Figure 20:
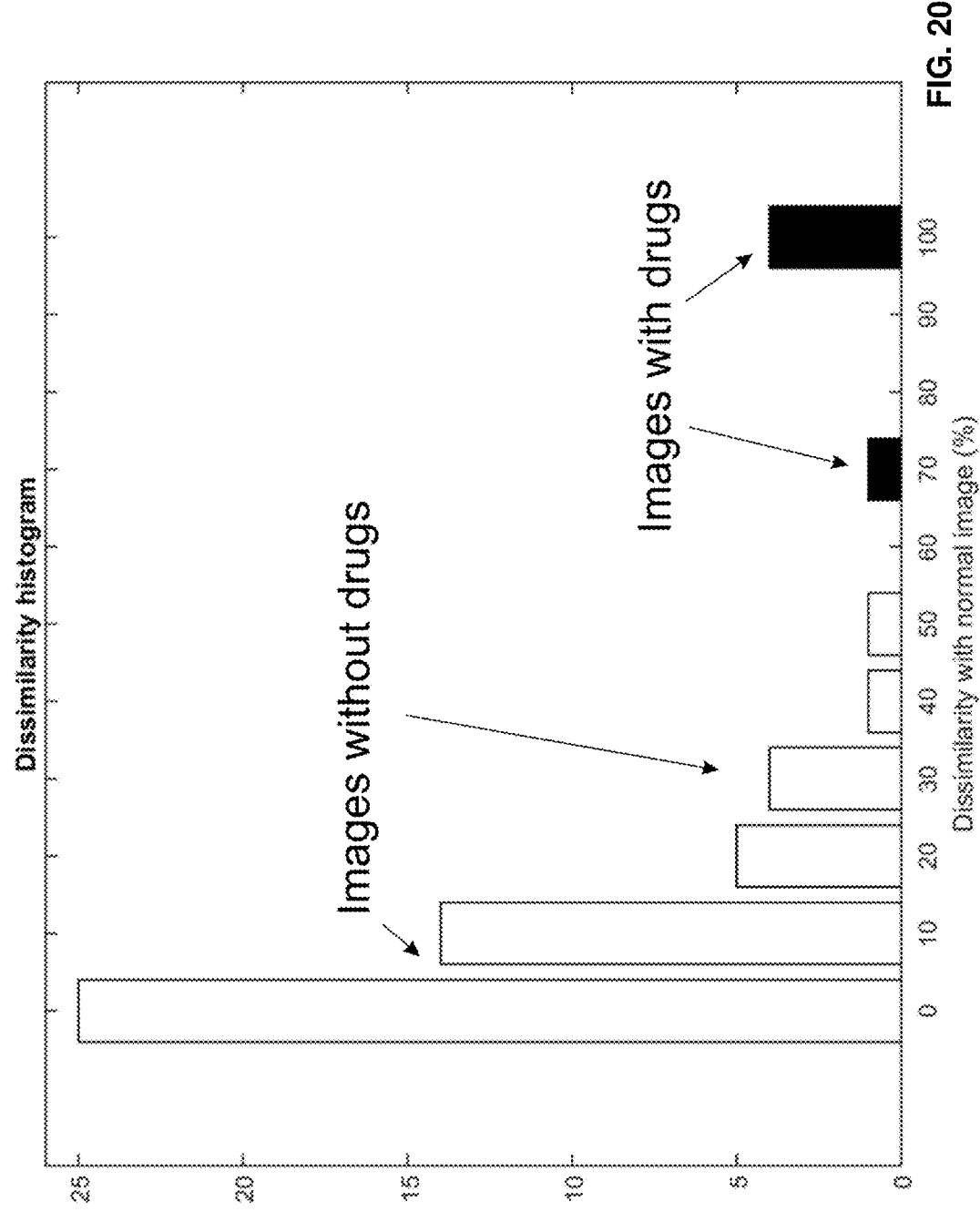
FIG. 20 illustrates a dissimilarity histogram.

An example of the transformation function $p(f/f_{max})$ with the parameter γ=0.1 is depicted in FIG. 19. Function p(x) provides for a more convenient way of selection of additional thresholds for separating groups of snapshots with different amounts of drugs (see FIG. 20) and also allows for analyzing of the algorithm precision. For example, groups of snapshots with large and small amounts of drugs can be defined using the thresholds of the function p(x).

Figure 3:
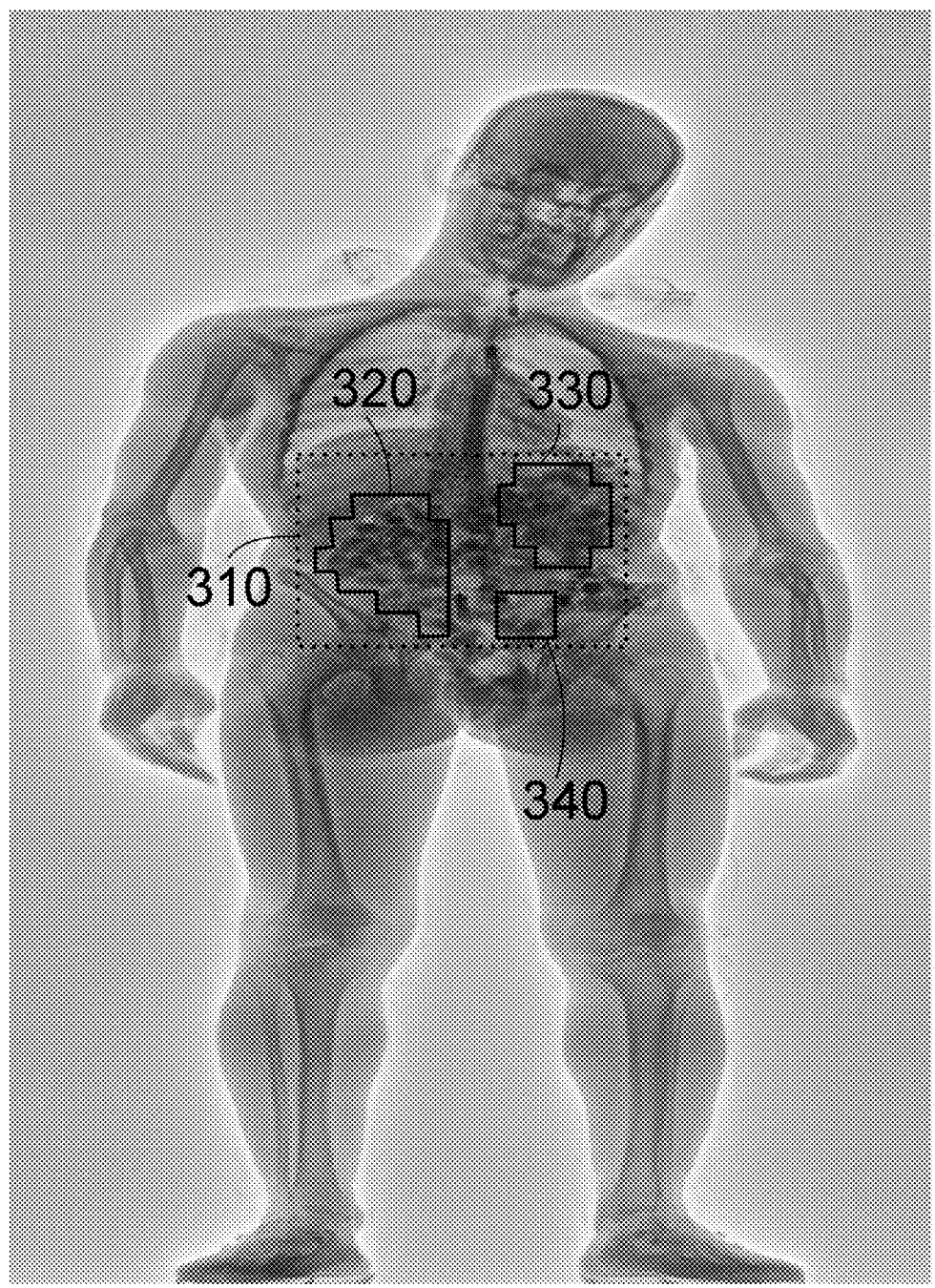
FIG. 3 illustrates and example of a contrasted image with detected suspicious areas.

FIG. 16 illustrates a flow chart for classifying the image for presence of drugs. In step 1610, the process constructs a windows' intersections map for windows suspected for presence of drugs. The intersections map with a certain minimal level of intersections (e.g., 2 or 3) can be used for visualization of areas suspected for presence of drugs. In this case, the operator is shown either the area where the number of intersections is greater or equals to a pre-set threshold or the area is broadened by dilation with one possible structural element. An example of the suspected areas 320, 330 and 340 with the intersection threshold 2 on the stomach 310 is depicted in FIG. 3.

In step 1620, the process calculates features from windows' intersections map. In step 1630, the process calculates features from the margins of the suspected windows and classifies the picture (snapshot) using the features in step 1640. The selected features, a value of the transformation parameters and the covariance matrix are used for calculation of the degree of difference of the snapshot from the average normal image (without drugs) using the above formulas. The calculated degree of difference (i.e., dissimilarity) is used for classification of the image using a rule for comparison to the threshold value. If the threshold reached or exceeded, the drugs are detected on the image. The threshold value is set at 50%.

Having thus described the different embodiments of a system and method, it should be apparent to those skilled in the art that certain advantages of the described method and apparatus have been achieved. In particular, it should be appreciated by those skilled in the art that the proposed method provides for an efficient detection of drugs located inside person's stomach.

It should also be appreciated that various modifications, adaptations, and alternative embodiments thereof may be made within the scope and spirit of the present invention. The invention is further defined by the following claims.

BIBLIOGRAPHY the publications below are incorporated by reference in their entirety:
Bishop, C. M. (2006), *Pattern Recognition and Machine Learning*, Springer.
Cortes, C., and V. Vapnik (1995), Support-vector networks, *Mach Learn*, V. 20(3), P. 273-297.
Drouin, S., R. Poulin, L. Perron, and D. Gudmundson (2015), US20150010128 A1: Method and system for identifying a liquid product in luggage or other receptacle.
Duta, N., A. K. Jain, and M. P. Dubuisson-Jolly (2001), Automatic construction of 2D shape models, *Pattern Analysis and Machine Intelligence*, IEEE Transactions on, V. 23(5), P. 433-446.
Flusser, J., and T. Suk (1993), Pattern recognition by affine moment invariants, *Pattern Recognition*, V. 26(1), P. 167-174.
Gupta, L., and M. D. Srinath (1987), Contour sequence moments for the classification of closed planar shapes, *Pattern Recognition*, V. 20(3), P. 267-272.
Haralick, R. M., K. Shanmugam, and I. H. Dinstein (1973), Textural Features for Image Classification, *Systems, Man and Cybernetics, IEEE Transactions on*, V. SMC-3(6), P. 610-621.
Hu, M.-K. (1962), Visual pattern recognition by moment invariants, *Information Theory, IRE Transactions on*, V. 8(2), P. 179-187.
Jain, A. K., R. P. W. Duin, and M. Jianchang (2000), Statistical pattern recognition: a review, *Pattern Analysis and Machine Intelligence*, IEEE Transactions on, V. 22(1), P. 4-37.
Kumar, A., and G. K. H. Pang (2002), Defect detection in textured materials using Gabor filters, *Industry Applications, IEEE Transactions on*, V. 38(2), P. 425-440.
Laurikkala, J., M. Juhola, and E. Kentala (2000), Informal Identification of Outliers in Medical Data, *paper presented at 5th International Workshopon Intelligent Data Analysis in Medicineand Pharmacology*, Berlin, Germany.
Lehmann, L. A., R. E. Alvarez, A. Macovski, W. R. Brody, N. J. Pelc, S. J. Riederer, and A. L. Hall (1981), Generalized image combinations in dual KVP digital radiography, *Medical Physics*, V. 8(5), P. 659-667.
Mery, D. (2011), Automated Detection of Welding Discontinuities without Segmentation, *Materials Evaluation*, P. 657-663.
Mery, D., and M. A. Berti (2003), Automatic detection of welding defects using texture features, *Insight—Non-Destructive Testing and Condition Monitoring*, V. 45(10), P. 676-681.
Mery, D., R. R. da Silva, L. P. CaMa, and J. M. A. Rebello (2003), Pattern recognition in the automatic inspection of aluminium castings, *Insight—Non-Destructive Testing and Condition Monitoring*, V. 45(7), P. 475-483.

Montabone, S., and A. Soto (2010), Human detection using a mobile platform and novel features derived from a visual saliency mechanism, *Image and Vision Computing*, V. 28(3), P. 391-402.

Ojala, T., M. Pietikainen, and T. Maenpaa (2002), Multiresolution gray-scale and rotation invariant texture classification with local binary patterns, *Pattern Analysis and Machine Intelligence, IEEE Transactions on*, V. 24(7), P. 971-987.

Saisan, P. (2013), U.S. Pat. No. 8,437,556 B1: Shape-based object detection and localization system.

Sun, Y., X. Wang, L. Wang, Y. Yi, and M. Chen (2014), U.S. Pat. No. 8,774,460 B2: Method of processing body inspection image and body inspection apparatus.

Vaidya, N. M. (2014), U.S. Pat. No. 8,774,461 B2: Method and system for automatic detection of a class of objects.

Yu, Z., and C. Bajaj (2004), A fast and adaptive method for image contrast enhancement, *paper presented at Image Processing, 2004. ICIP '04. 2004 International Conference on,* 24-27 Oct. 2004.

Zuiderveld, K. (1994), Contrast Limited Adaptive Histograph Equalization, in *Graphic Gems IV*, edited, pp. 474-485, Academic Press Professional, San Diego.

What is claimed is:

1. A method for an automated detection of swallowed capsules on X-ray scanner images, the method comprising:
   (a) acquiring an incoming image of a person passing through the scanner;
   (b) generating additional images based on the incoming image by performing transformations of the incoming image;
   (c) determining an upper body area on the incoming image;
   (d) calculating a position of a stomach area on the upper body area of the incoming image and on the additional images;
   (e) classifying segmented regions of the stomach area of the incoming image;
   (f) calculating geometrical and intensity features along with rotationally invariant periodic features for windows on the stomach area;
   (g) detecting suspected windows on the stomach area;
   (h) calculating aggregate features for the properties of the suspected windows;
   (i) using a model for the images that do not contain swallowed capsules classifying the incoming image using a threshold for a dissimilarity function; and
   (j) informing a user that the incoming image contains the swallowed capsules if the dissimilarity function for aggregate features for the incoming image is larger than or equal to the threshold.

2. The method of claim 1, wherein periodic features is used to calculate the rotationally invariant features in such a way that same horizontal, vertical or diagonal periodicity produce an input into one common property.

3. The method of claim 1 further comprising segmenting the stomach area prior to the calculating of geometrical and intensity features along with rotationally invariant periodic features for windows on stomach area.

4. The method of claim 1, further comprising:
   building a windows' intersection map for windows suspected for presence of swallowed capsules; and
   calculating aggregate features from the windows' intersection map.

5. The method of claim 1, wherein the additional images that are generated from the incoming image are any of:
   logarithmic images;
   contrasted images; and
   saliency map images.

6. The method of claim 1, wherein aggregate features are constructed from the margin values for separating images with swallowed capsules and images without swallowed capsules.

7. The method of claim 6, wherein the aggregate stomach area features are any of:
   a sum of margins to a dividing hyper-plane;
   an average value of the margins to a dividing hyper-plane; and
   standard deviation of the margins to a dividing hyper-plane.

8. The method of claim 6, wherein the aggregate stomach area features are any of:
   1-st maximum absolute value of the margin to a dividing hyper-plane;
   2-d maximum absolute value of the margin to a dividing hyper-plane;
   3-d maximum absolute value of the margin to a dividing hyper-plane;
   4-th maximum absolute value of the margin to a dividing hyper-plane;
   5-th maximum absolute value of the margin to a dividing hyper-plane;
   a sum of 5 maximum margins to a dividing hyper-plane; and
   an average value of 5 maximum margins to a dividing hyper-plane.

9. The method of claim 1, wherein the model of images without swallowed capsules is a multivariate image model constructed based on a multivariate normal distribution described by a covariance matrix of training data set.

10. The method of claim 1, further comprising calculating any of geometric features for segmented areas:
    a relative vertical coordinate of a center of an area calculated as a fraction of an average of a row numbers of all area points of the stomach area over a height of the stomach;
    a relative horizontal coordinate of a center of an area calculated as a distance from a calculated area center to a middle of the stomach divide by a half of a stomach width;
    a length of an area along a horizontal and a vertical directions;
    a number of pixels inside an area; and
    a number of pixels located on a border of an area and a background.

11. The method of claim 1, wherein the geometric features are any of:
    geometric features invariant relative to translations, scale and rotations;
    geometric features invariant relative to common affine transformations;
    geometric features of area borders invariant to displacements, scale and rotations.

12. The method of claim 1, further comprising calculating any of the following intensity features:
    integral, average and maximum values of intensity, gradient and laplacian;
    features of image texture; and
    features used for texture description on different scales and in different directions.

13. The method of claim 1, wherein a sum of selected rotationally invariant periodic features is used for constructing the classifier.

14. The method of claim 1, further reducing the dimensionality of training data by using one of the state of art selecting features method.

15. The method of claim 1, further comprising generating the model for images that do not contain swallowed capsules based on training data set.

16. The method of claim 1, further comprising constructing a classifier based on geometric and intensity features along with rotationally invariant periodic features of images.

17. The method of claim 1, further comprising informing the user that the incoming image does not contain swallowed capsules if dissimilarity function value for aggregate features for the current incoming image is below the threshold.

18. The method of claim 1, wherein the additional images are generated in order to analyze a larger pool of image features.

19. The method of claim 1, further comprising removing the high-contrast objects from the stomach area image.

20. The method of claim 1, further comprising selecting parameters for a windows' classifier based on the window features for multiple images from a training database; and
constructing the windows' classifier based on the parameters.

21. The method of claim 1, further comprising calculating margin values of the suspected windows, after step (g).

22. The method of claim 1, further comprising subtracting high-contrast objects from stomach area of the incoming and additional images, after step (e).

23. A system for an automated detection of swallowed capsules on X-ray scanner images comprising:
an X-ray scanner;
a processing unit connected to the X-ray scanner and configured to receive and process an image from the X-ray scanner;
a monitor connected to the processing unit configured to display image to an operator wherein:
the processing unit identifies a stomach area on the image;
the processing unit classifies segmented regions of the stomach area of the incoming image on high-contrast objects and background;
the processing unit subtracts high-contrast objects from stomach area of the incoming image;
the processing unit calculates geometrical and intensity features along with rotationally invariant periodic features of windows on the stomach area;
the processing unit detects suspected windows on the stomach area;
the processing unit calculates windows' margin values and aggregate features for the margins of suspected windows;
the processing unit classifies the image based on a threshold for dissimilarity function value defined by the image aggregate features in order to detect images having the swallowed capsules; and
the processing unit informs the operator when the swallowed capsules are detected in the stomach area.

24. A method for an automated detection of swallowed capsules on X-ray scanner images, the method comprising:
(a) acquiring an incoming image of a person passing through the scanner;
(b) generating additional images by performing transformations of the incoming image;
(c) determining a position of a stomach area on the incoming image and on the additional images;
(d) classifying segmented regions of the stomach area of the incoming image;
(e) calculating geometrical and intensity features along with rotationally invariant periodic features for windows on the stomach area;
(f) detecting suspected windows on the stomach area;
(g) calculating aggregate features for the properties of the suspected windows;
(h) using the model for the images that do not contain swallowed capsules for classifying the incoming image using a threshold for a dissimilarity function; and
(i) informing a user that the incoming image contains the swallowed capsules based on step (h).

25. A method for an automated detection of swallowed capsules on X-ray scanner images, the method comprising:
(a) based on an incoming image of a person passing through the scanner, generating a transformed image from the incoming image;
(b) calculating a position of a stomach area on the incoming image and on the transformed image;
(c) classifying segmented regions of the stomach area of the incoming image;
(d) calculating rotationally invariant periodic features for windows on the stomach area;
(e) detecting suspected windows on the stomach area;
(f) calculating aggregate features for the suspected windows; and
(g) using a model for images that do not contain swallowed capsules, informing a user of the swallowed capsules if a dissimilarity function for the aggregate features is equal to or above a predefined threshold.

* * * * *